United States Patent [19]

Huppatz et al.

[11] Patent Number: 4,935,052
[45] Date of Patent: Jun. 19, 1990

[54] HERBICIDAL CRONTONIC ACID DERIVATIVES, THEIR PREPARATION AND COMPOSITIONS CONTAINING THEM

[75] Inventors: John L. Huppatz, Weetangera; John N. Phillips, Yarralumla, both of Australia

[73] Assignee: Commonwealth Scientific and Industrial Research Organization, Australia

[21] Appl. No.: 77,055

[22] Filed: Jul. 21, 1987

Related U.S. Application Data

[63] Continuation of Ser. No. 726,246, filed as PCT AU84/00145 on Jul. 26, 1984, published as WO85/00598 on Feb. 14, 1985, abandoned.

[30] Foreign Application Priority Data

Jul. 29, 1983 [AU] Australia ............... PG/0581

[51] Int. Cl.$^5$ ............... A01N 33/06; C07C 119/00
[52] U.S. Cl. ........................ 71/105; 558/390
[58] Field of Search ............... 558/390; 71/105

[56] References Cited

U.S. PATENT DOCUMENTS 3,981,717 9/1976 Walworth .................. 71/105
4,508,659 4/1985 Rowson et al. .......... 260/465 D Primary Examiner—Mary C. Lee
Assistant Examiner—J. Richter
Attorney, Agent, or Firm—Sughrue, Mion, Zinn, Macpeak & Seas

[57] ABSTRACT

Crotonic acid derivatives of the formula

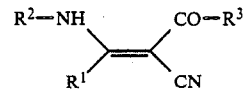

wherein
$R^1$ is optionally substituted alkyl or optionally substituted aryl;
$R^2$ is alkyl, cycloalkyl, optionally substituted phenylalkyl or heterocyclic substituted alkyl;
$R^3$ is alkyl, optionally substituted alkoxy, alkenyloxy, alkynyloxy, optionally substituted aryloxy, optionally substituted phenylalkyl or optionally substituted amino.

The compounds are useful as selective post-emergent herbicides.

12 Claims, No Drawings

HERBICIDAL CROTONIC ACID DERIVATIVES, THEIR PREPARATION AND COMPOSITIONS CONTAINING THEM

This is a continuation of application Ser. No. 726,246, filed as PCT AU84/00145 on Jul. 26, 1984, published as WO85/00598 on Feb. 14, 1985 now abandoned.

TECHNICAL FIELD

This invention relates to new crotonic acid derivatives and to compositions comprising the new derivatives. These compounds and compositions are of use as post-emergent herbicides.

BACKGROUND ART

Compounds which are known to affect the photosynthesis process have proved useful in agriculture as selective herbicides. The majority of these known compounds are non-toxic to mammals and present few environmental problems since they are specific to a process which is unique to plant life. In view of these advantages, interference with the photosynthetic process is an attractive target for the design of new herbicides.

A study of the mechanism of photosynthetic electron transport by the present invention has enabled compounds to be developed which inhibit electron transport at the same site as the commercially available herbicides such as diuron (DCMU), the triazines and bromacil. The compounds of the present invention are chemically distinct from these known compounds, and are further distinguished from known classes of photosynthetic herbicides by their almost exclusive post-emergent action and the unique selectivity pattern that they display.

DISCLOSURE OF THE INVENTION

It is an object of the present invention to provide novel derivatives of crotonic acid esters and amides and related compounds which exhibit useful post-emergent herbicidal activity.

According to a first aspect of the present invention there are provided compounds of the formula (I):

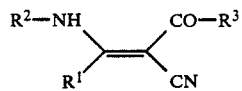
(I)

wherein, $R^1$ is a radical selected from the group consisting of alkyl, substituted alkyl, aryl and substituted aryl;

$R^2$ is (a) a radical selected from the group consisting of alkyl and cycloalkyl, (b) a radical of the formula (II):

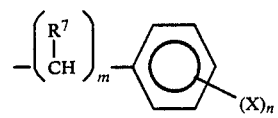
(II)

wherein, $R^7$ is a radical selected from the group consisting of hydrogen, alkyl, aralkyl and substituted aralkyl, m is an integer selected from the range 1 to 4, n is an integer selected from the range 1 to 3, X is a radical selected from the group consisting of hydrogen, alkyl, substituted alkyl, alkenyl, alkynyl, alkoxy, aryl, substituted aryl, halogen, trifluoromethyl, thiocyanato, nitro, cyano, amino, carboxy, alkoxycarbonyl, thioalkyl, carbamoyl, amido, N-alkylcarbamoyl, N,N-dialkylcarbamoyl, sulphonamido and a radical of the formula (III):

(III)

wherein, r is 0 or an integer selected from the range 1 to 4 and Ph is aryl or substituted aryl, (c) a radical of the formula (IV):

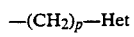
(IV)

wherein, p is an integer selected from the range 1 to 4 and Het is a heterocyclic moiety;

$R^3$ is (a) alkyl, (b) —$OR^4$ wherein $R^4$ is a radical selected from the group consisting of alkyl, alkenyl, alkynyl, aryl and substituted aryl, (c) a group of the formula (II) as hereinbefore defined, (d) a group of the formula (V):

(V)

wherein, q is an integer selected from the range 1 to 4, and Y is a radical selected from the group consisting of halogen, hydroxy, alkoxy, aryloxy, aryl, substituted aryl, acyloxy, thiocyanato, nitro, cyano, amino, substituted amino and a heterocyclic moiety, (e) —$NR^5R^6$ wherein $R^5$ and $R^6$ are radicals separately selected from the group consisting of hydrogen, alkyl, alkenyl, alkynyl, substituted alkyl, alkoxy, aryloxy, aryl, substituted aryl.

As used throughout the specification, the terms "alkyl", "substituted alkyl", "aryl", "cycloalkyl", "alkenyl", "alkynyl", 'alkoxy", "substituted aryl", "aryloxy", "heterocyclic", "aralkyl", "substituted aralkyl", "acyloxy" are used to denote the following:

"alkyl"

straight- or branched-chain hydrocarbons of 1 to 10, preferably 1 to 8, carbon atoms;

"acyloxy"

radicals in which the acyl portion is derived from a carboxylic or sulphonic acid; a preferred example is acetoxy;

"cycloalkyl"

alicyclic rings containing from 3 to 10 carbon atoms; preferred examples are cyclopropyl, cyclopentyl and cyclohexyl;

"alkenyl"

radicals in which the hydrocarbon portion is a straight or branched chain of 1 to 10 carbon atoms, unsubstituted or substituted by one or more radicals separately selected from the group consisting of hydroxy, halogen, amino, alkoxy, N-alkylamino and N,N-dialkylamino;

"aryl"

6- or more-membered aromatic rings, which may or may not be fused to aliphatic or aromatic rings; preferred examples include benzene, naphthalene, indene and tetrahydronaphthalene;

"heterocyclic"

5- or 6-membered aliphatic or aromatic rings containing at least one hetero atom selected from O, N and S, unsubstituted or substituted by one or more radicals separately selected from the group consisting of alkyl, hydroxy, carboxy and halogen; preferred examples include furan, thiophene, piperidine, pyrrole and pyridine;

"substituted aryl"

aryl rings substituted by one or more radicals separately selected from the group consisting of alkyl, substituted alkyl, halogen, hydroxy, alkoxy, amino, N-alkylamino and N,N-dialkylamino;

"substituted alkyl"

alkyl radicals substituted by one or more radicals separately selected from the group consisting of hydroxy, amino, N-alkylamino, N,N-dialkylamino, alkoxy or halogen;

"alkynyl"

radicals in which the hydrocarbon portion is a straight- or branched-chain of 1 to 10 carbon atoms, unsubstituted or substituted by one or more radicals separately selected from the group consisting of hydroxy, alkoxy, halogen, amino, N-alkylamino and N,N-dialkylamino;

"alkoxy"

radicals in which the alkyl portion is a straight- or branched-chain hydrocarbon of 1 to 10 carbon atoms;

"aryloxy"

radicals in which the aryl ring is unsubstituted or substituted by one or more radicals separately selected from the group consisting of alkyl, substituted alkyl, hydroxy, amino, alkoxy, halogen, N-alkylamino and N,N-dialkylamino; a preferred example is phenoxy;

"aralkyl"

radicals in which the aromatic and aliphatic portions are an aryl ring and an alkyl radical respectively, both as hereinbefore defined;

"substituted aralkyl"

radicals in which the aromatic and/or aliphatic portions are a substituted aryl ring and/or a substituted alkyl radical respectively, both as hereinbefore defined;

It will be appreciated that some of the compounds referred to throughout this specification are chiral and the present invention relates both to the individual stereoisomers and to any mixtures thereof whether these mixtures include enantiomers and/or diastereoisomers.

According to a second aspect of the present invention, there is provided a process for the preparation of compounds of the formula (I):

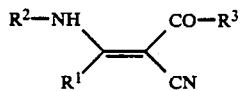

(I)

wherein $R^1$, $R^2$ and $R^3$ are as hereinbefore defined, comprising the reaction of a crotonic acid derivative of formula (VI):

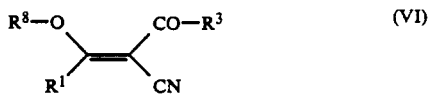

(VI)

wherein $R^8$ represents methyl or ethyl, and $R^3$ is as hereinbefore defined, with a compound of the formula (VII):

wherein $R^2$ is as hereinbefore defined.

Preferably, $R^1$ is selected from the group consisting of $C_1$–$C_4$ alkyl, hydroxyalkyl, alkoxyalkyl, haloalkyl, phenyl or substituted phenyl; $R^2$ is (a) alkyl or cycloalkyl, (b) a radical of formula (II) wherein $R^7$ is selected from the group consisting of hydrgen, $C_1$–$C_4$ alkyl, benzyl and substituted benzyl, and X is selected from the group consisting of hydrogen, $C_1$–$C_8$ alkyl, alkenyl, alkynyl, hydroxyalkyl, alkoxyalkyl, alkoxy, substituted phenyl, halogen, trifluoromethyl, thiocyanato, nitro, cyano, amino, carboxy, alkoxycarbonyl, carbamoyl, N-alkylcarbamoyl, N,N-dialkylcarbamoyl, (c) a radical of formula (III) wherein Ph is substituted phenyl; $R^3$ is (a) $C_1$–$C_4$ alkyl, (b) —$OR^4$ wherein $R^4$ is a radical selected from the group consisting of $C_1$–$C_4$ alkyl, alkenyl, alkynyl, phenyl and substituted phenyl, (c) a group of the formula (II) wherein $R^7$ and X are as hereinbefore defined with respect to the preferred identity of $R^2$, (d) a group of the formula (V) wherein Y is a radical selected from the group consisting of halogen, hydroxy, alkoxy, phenoxy, substituted phenoxy, phenyl, substituted phenyl, thiocyanato, nitro, cyano, amino and heterocyclic moiety, (e) —$NR^5R^6$ wherein $R^5$ and $R^6$ are separately selected from the group consisting of hydrogen, $C_1$–$C_8$ alkyl, alkenyl, alkynyl, hydroxyalkyl, alkoxyalkyl, alkoxy, phenoxy, substituted phenoxy, phenyl and substituted phenyl.

More preferably, $R^1$ is ethyl, $R^2$ is 4-chlorobenzyl and $R^3$ represents a group of the formula (V) wherein q is 2 and Y is an ethoxy radical.

Compounds of the general formulae (VI) and (VII) are either known, or can be prepared from known compounds by standard reactions well known in the art. For example, compounds of formula (VI) can be prepared following a similar procedure to that described by Huppatz et al, *Agri. Biol. Chem.*, 45, 2769 (1981) or by Hayashi et al, *J. Org. Chem.* 30, 395 (1965).

The general method for preparing compounds of formula (I) comprises the reaction of a compound of formula (VI) with a compound of formula (VII) at room temperature. Although the reaction proceeds without the application of external heat, it is preferably carried out at 100° C. for 30 minutes.

It has been found that the compounds of formula (I) generally have an excellent herbicidal activity against a number of plant species.

In practice, the compounds of the present invention are not generally employed by themselves. More frequently, they are used in compositions which generally comprise, in addition to the active ingredient, an inert carrier or diluent.

Accordingly, a third aspect of the present invention is the provision of herbicidal compositions which include at least one of the compounds of formula (I) as an active ingredient, and the application of such compositions to control the growth of undesirable plant species.

The method of controlling the growth of undesirable plant species comprises applying to the plants, seeds or soil an effective amount of a composition containing at least one compound of formula (I). The term "effective amount" is understood as meaning a sufficient amount to enable undesirable plant species to be controlled and destroyed. However, the application rates used can vary within wide limits, according to the plant species to be combated, the type of crop, the climatic conditions and the particular compound used.

Compounds of the present invention have been tested for herbicidal activity against a number of plant species. In particular, they have been tested against the following plant species: white mustard (*Sinapsis alba*), barley (*Hordeum vulgare*) v. Cape, *Amaranthus edulis*, rape (*Brassica napus*) v. napus, linseed (*Linum usitatissimum*) v. Glenelg, ryegrass (*Lolium perenne*) v. N.Z. subterranean clover (*Trifolium subterraneum*) v. Tallarook, Johnson grass (*Sorghum halepense*) Wimmera ryegrass (*Lolium rigidum*), sorghum (*Sorghum bicolor*), barnyard grass (*Echinochloa crus-galli*), rice (*Oryza sativa*) v. Calrose, beans (*Phaseoulus vulgaris*) v. Windsor long pod, wheat (*Triticum aestivum*) v. Teal, oats (*Avena sativa*) v. Coolabah, sugar beet (*Beta vulgaris* ssp vulgaris) lupins (*Lupinus albus*) v. Uniwhite, guinea grass (*Panicum maximum*), Japanese millet (*Echinochloa utilis*), peas (*Pisum sativum*) v. Victory freezer, maize (*Zea mays*) v. PX744.

As mentioned above, the compounds of the present invention are usually admixed with an inert carrier or diluent. In the present specification, the term "carrier or diluent" denotes an organic or inorganic, natural or synthetic material with which the active ingredient is combined in order to facilitate its application to the plant, to the seeds or to the soil. This carrier or diluent is therefore generally inert and it must be acceptable in agriculture, in particular on the plant treated. The carrier or diluent can be solid (clays, natural or synthetic silicates, silica, chalks, resins, waxes, solid fertilisers and the like) or liquid (water, alcohols, ketones, petroleum ctions, aromatic or paraffinic hydrocarbons, chlorohydrocarbons, liquefied gases and the like).

The compositions of the invention can be in a wide variety of solid or liquid forms.

As forms of solid compositions there may be mentioned dusting powders.

As forming of liquid compositions or compositions which are to be made up into liquid compositions on application, there may be mentioned solutions, in particular water-soluble concentrates, emulsifiable concentrates, emulsions, suspension concentrates, aerosols, wettable powders (or spraying powders) and pastes.

In addition to the solvent, and where necessary, the emulsifiable concentrates can contain a suitable co-solvent and suitable additives, such as stabilisers and antifoam agents.

DETAILED DESCRIPTION OF EMBODIMENTS

Specific details of the compounds of the present invention, the reactions involved in the processes of this invention, and the use of the compounds of the present invention are illustrated by the following examples. In these examples, all temperatures are in degrees Centrigrade, and technical terms have the usual meaning in the art. Crude reaction products can be purified by the means described herein, or by other means known in the art.

EXAMPLE 1 ethoxyethyl 2-cyano-3-dl-α-methylbenzylamino-3-ethylacrylate

Ethoxyethyl 2-cyano-3-ethoxy-3-ethylacrylate (1.2 g) (prepared from ethoxyethyl cyanoacetate, triethyl orthopropionate and acetic anhydride) and dl-α-methylbenzylamine (0.6 g) were heated together in an oil bath at 100°-110° C. for 30 minutes. Distillation of the product mixture afforded ethoxyethyl 2-cyano-3-dl-α-methylbenzylamino-3-ethylacrylate (1.4 g) as a pale yellow oil, b.p. 196°-198° C./0.1 mm.

EXAMPLE 2 ethoxyethyl 2-cyano-3-(4-chlorobenzylamino) crotonate

Ethoxyethyl 2-cyano-3-ethoxycrotonate (2.3 g) (prepared from ethoxyethyl cyanoacetate, triethyl orthoacetate and acetic anhydride) and 4-chlorobenzylamine (1.4 g) were heated together in an oil bath at 100°-110° C. for 30 minutes. After cooling, the product was crystallised from ethyl acetate-petroleum ether (b.p. 40°-60° C.) to afford ethoxyethyl 2-cyano-3-(4-chlorobenzylamino) crotonate (2.7 g) as colourless needles, m.p. 72°-73° C.

EXAMPLE 3 cyanoethyl 2-cyano-3-(4-chlorobenzylamino) crotonate

Cyanoethyl 2-cyano-3-ethoxycrotonate (1.9 g) (prepared from cyanoethyl cyanoacetate, triethyl orthoacetate and acetic anhydride) and 4-chlorobenzylamine (1.4 g) were heated together in an oil bath at 90°-100° C. for 30 minutes. After cooling, the product was crystallised from ethyl acetate to afford cyanoethyl 2-cyano-3-(4-chlorobenzylamino) crontonate (2.5 g) as colourless needles, m.p. 111°-113° C.

EXAMPLE 4 ethoxyethyl 2-cyano-3-(4-chlorobenzylamino)-3-ethylacrylate

Ethoxyethyl 2-cyano-3-ethoxy-3-ethylacrylate (2.4 g) (prepared from ethoxyethyl cyanoacetate, triethyl orthopropionate and acetic anhydride) and 4-chlorobenzylamine (1.4 g) were heated together in an oil bath at 100°-110° C. for 30 minutes. After cooling, the product was crystallised from ethyl acetate-petroleum ether (b.p. 40°-60° C.) to afford ethoxyethyl 2-cyano-3-(4-chlorobenzylamino-3-ethylacrylate (3.0 g) as colourless needles, m.p. 56°-57° C.

EXAMPLE 5

Tables I-V list novel compounds of the formula (I) prepared by similar methods to those described in Examples 1-4.

TABLE I

COMPOUNDS OF FORMULA:

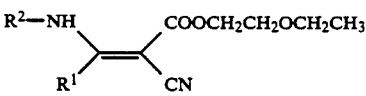

| COMPOUND NO | R¹ | R² | M.p. (°C.)/B.p. (mm) |
|---|---|---|---|
| 1 | $CH_3$ | $C_8H_{17}$ | 186–188 (0.05) |
| 2 | $C_2H_5$ | " | 193–194 (0.05) |
| 3 | $C_3H_7$ | " | 191–192 (0.01) |
| 4 | $C_4H_9$ | " | 195–197 (0.01) |
| 5 | Ph | " | 220–222 (0.1) |
| 6 | $C_2H_5$ | $C_4H_9$ | 164–165 (0.1) |
| 7 | $CH_3$ | $C_{10}H_{21}$ | 207–208 (0.1) |
| 8 | $C_2H_5$ | " | 204–205 (0.1) |
| 9 | Ph | $CH_3$ | 81–84 |

TABLE II

COMPOUNDS OF FORMULA:

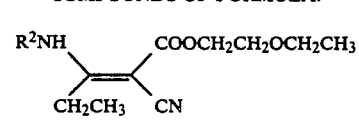

| COMPOUND NO. | R² | M.p. (°C.)/B.p. (mm) |
|---|---|---|
| 10 | (±)$PhCH(CH_3)$— | 196–198 (0.1) |
| 11 | $CH_3CH(CH_3)$— | 172–174 (0.6) |
| 12 | $C_2H_5CH(CH_3)$— | 156–158 (0.1) |
| 13 | $C_3H_7CH(CH_3)$— | 161–162 (0.05) |
| 14 | $C_5H_{11}CH(CH_3)$— | 195–197 (0.5) |
| 15 | $C_6H_{13}CH(CH_3)$— | 180–182 (0.1) |
| 10a | $R(-)PhCH(CH_3)$— | 194–196 (0.1) |
| 10b | $S(+)PhCH(CH_3)$— | 195–197 (0.1) |

TABLE III

COMPOUNDS OF FORMULA:

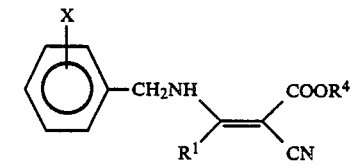

| COMPOUND NO. | R¹ | R⁴ | X | M.p. (°C.)/B.p. (mm) |
|---|---|---|---|---|
| 16 | $CH_3$ | —$(CH_2)_2OC_2H_5$ | H | 198–200 (0.05) |
| 17 | " | " | 4-Cl | 72–73° |
| 18 | " | " | 3-Cl | 225–227 (0.05) |
| 19 | " | " | 3,4-$Cl_2$ | 98.5–100 |
| 20 | $C_2H_5$ | " | H | 35–37 |
| 21 | " | " | 2-Cl | 64–65 |
| 22 | " | " | 3-Cl | 65–66 |
| 23 | " | " | 4-Cl | 56–57 |
| 24 | " | " | 3-$CH_3$ | 58–59 |
| 25 | " | " | 4-$CH_3$ | 210–212 (0.05) |
| 26 | " | " | 2-$OCH_3$ | 206–208 (0.05) |
| 27 | $C_2H_5$ | —$(CH_2)_2OC_2H_5$ | 3-$OCH_3$ | 209–211 (0.05) |
| 28 | " | " | 4-$OCH_3$ | 213–215 (0.05) |
| 29 | " | " | 4-$NO_2$ | 84–86 |
| 30 | " | " | 3,4-$Cl_2$ | 62–64 |
| 31 | $C_3H_7$ | " | H | 201–203 (0.01) |
| 32 | " | " | 3-Cl | 217–219 (0.05) |
| 33 | " | " | 4-Cl | 215–217 (0.01) |
| 34 | $C_4H_9$ | " | H | 203–205 (0.01) |
| 35 | " | " | 3-Cl | 219–221 (0.01) |
| 36 | " | " | 4-Cl | 223–224 (0.01) |
| 37 | $C_2H_5$ | sec-$C_4H_9$ | 3-Cl | 196–198 (0.05) |
| 38 | " | " | 4-Cl | 67–68 |
| 39 | " | $C_3H_7$ | 3-Cl | 60–61 |

TABLE III-continued

COMPOUNDS OF FORMULA:

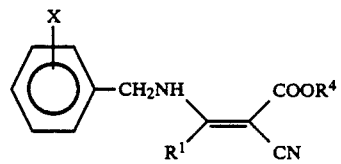

| COMPOUND NO. | R¹ | R⁴ | X | M.p. (°C.)/B.p. (mm) |
|---|---|---|---|---|
| 40 | " | " | 4-Cl | 76–77 |
| 41 | $C_2H_5$ | $C_2H_5$ | 3-Cl | 76–77 |
| 42 | " | " | 4-Cl | 80–81 |
| 43 | " | $CH_3$ | 3-Cl | 200–201 (0.05) |
| 44 | " | " | 4-Cl | 200–202 (0.05) |

TABLE IV

COMPOUNDS OF FORMULA:

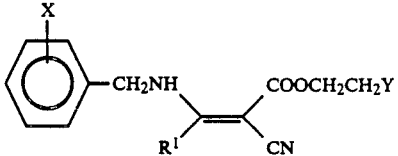

| COMPOUND NO. | R¹ | Y | X | M.p. (°C.)/B.p. (mm) |
|---|---|---|---|---|
| 45 | $CH_3$ | CN | 3-Cl | 91–92 |
| 46 | " | " | 4-Cl | 111–113 |
| 47 | $C_2H_5$ | " | H | 73–73.5 |
| 48 | " | " | 3-Cl | 85–86 |
| 49 | " | " | 4-Cl | 123–125 |
| 50 | " | " | 3,4-$Cl_2$ | 118–119 |
| 51 | " | $OCOCH_3$ | 4-Cl | 93–94 |
| 52 | " | OH | " | 98–99 |
| 53 | " | Cl | " | 111–112 |
| 54 | " | OPh | " | 72–75 |

TABLE V

COMPOUNDS OF FORMULA:

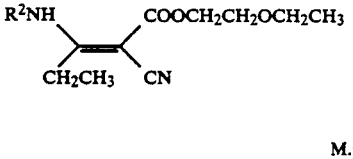

| COMPOUND NO. | R² | M.p. (°C.)/B.p. (mm) |
|---|---|---|
| 55 | —$CH_2$—(pyridyl-N) | 210–212 (0.01) |
| 56 | —$CH_2$—(pyridyl-N) | 214–216 (0.05) |
| 57 | —$CH_2$—(furyl-O) | 184–186 (0.05) |

TABLE V-continued

COMPOUNDS OF FORMULA:

$$\begin{array}{c} R^2NH \quad\quad COOCH_2CH_2OCH_2CH_3 \\ \diagdown C{=}C \diagup \\ \diagup \quad\quad \diagdown \\ CH_2CH_3 \quad\quad CN \end{array}$$

| COMPOUND NO. | R² | M.p. (°C.)/B.p. (mm) |
|---|---|---|
| 58 | −(CH₂)₂−C₆H₅ | 208–211 (0.1) |
| 59 | −(CH₂)₃−C₆H₅ | 216–218 (0.05) |
| 60 | −CH₂−C₆H₅ | 50–52 |
| 61 | −CH₂−C₆H₄−F | 56–58 |
| 62 | −CH₂−C₆H₄−Br | 64–66 |
| 63 | −CH₂−C₆H₄−NH₂ | oil |
| 64 | −CH₂−C₆H₄−SCH₃ | 57–59 |
| 65 | −CH₂−C₆H₄−CF₃ | 65–67 |
| 66 | −CH₂−C₆H₄−SO₂NH₂ | 130–131 |
| 67 | −CH₂−C₆H₄−NHCOCH₃ | 99–101 |
| 68 | −CH₂−C₆H₃(Cl)(Cl) | 62–63 |

EXAMPLE 6

Representative compounds listed in Tables I–V were tested for herbicidal activity against a number of plant species. Seeds of the test species were sown in rows in a thin layer of fine sand distributed over a 4 cm. layer of steam-sterilised soil contained in aluminium pans (20×10×7 cm) and the seedlings grown under fluorescent lights in a glass house (24 3° C.; 16,000 lux at surface; 12 hour photoperiod). The compounds were applied as a 50% acetone solution to 14 day old seedlings at a rate corresponding to 4 kg/ha. Herbicidal activity was assessed 14 days afteer spraying. A visual score was given to each plant species on a scale of 10 (complete kill) to 0 (no effect).

Compounds 10, 16, 20, 22, 23, 25 and 28 were tested against the following plant species: white mustard (*Sinapsis alba*), barley (*Hordeum vulgare*), v. Cape, *Amaranthus edulis*, rape (*Brassica napus*) v. napus, linseed (*Linum usitatissimum*) v. Glenelg, ryegrass (*Lolium perenne*) v. N.Z. subterranean clover (*Trifolium subterraneum*) v. Tallarook, Johnson grass (*Sorghum halepense*) Wimmera ryegrass (*Lolium rigidum*), sorghum (*Sorghum bicolor*), barnyard grass (*Echinochloa crusgalli*) rice (*Oryza sativa*) v. Calrose, beans (*Phaseoulus vulgaris*) v. Windsor long pod, wheat (*Triticum aestivum*) v. Teal, oats (*Avena sativa*) v. Coolabah, sugar beet (*Beta vulgaris* ssp vulgaris), lupins (*Lupinus albus*) v. Uniwhite, guinea grass (*Panicum maximum*) and Japanese millet (*Echinochloa utilis*).

Compounds 1, 2, 7, 8, 14, 41, 42, 43, 44, 58 and 59 were tested against peas (*Pisum sativum*) v. Victory freezer, white mustard (*Sinapsis alba*), barley (*Hordeum vulgare*) v. Cape, maize (*Zea mays*) v. PX744, linseed (*Linum usitatissimum*) v. Glenelg and ryegrass (*Lolium perenne*) v. N.Z.

The effects of these represetative compounds on the various plant species are detailed in Table VI.

TABLE VI

| Plant Species | Compound No. | | | | | | |
|---|---|---|---|---|---|---|---|
| | 10 | 16 | 20 | 22 | 23 | 25 | 28 |
|---|---|---|---|---|---|---|---|
| White mustard | 10 | 10 | 6 | 10 | 10 | 10 | 9 |
| Barley | 5 | 1 | 3 | 2 | 4 | 2 | 2 |
| Amaranthus | 10 | 10 | 10 | 10 | 10 | 10 | 10 |
| Rape | 10 | 4 | 10 | 10 | 10 | 10 | 3 |
| Linseed | 10 | 4 | 8 | 10 | 10 | 9 | 10 |
| Ryegrass | 6 | 3 | 2 | 0 | 2 | 0 | 0 |
| Sub-clover | 10 | 2 | 2 | 2 | 2 | 3 | 3 |

TABLE VI-continued

| | | | | | | | |
|---|---|---|---|---|---|---|---|
| Johnson grass | 2 | 2 | 2 | 4 | 2 | 3 | 2 |
| Wimmera ryegrass | 5 | 3 | 2 | 0 | 2 | 2 | 2 |
| Sorghum | 3 | 1 | 0 | 0 | 2 | 1 | 0 |
| Barnyard grass | 3 | 2 | 2 | 3 | 1 | 2 | 0 |
| Rice | 3 | 2 | 0 | 4 | 0 | 2 | 0 |
| Beans | 10 | 2 | 1 | 3 | 3 | 2 | 0 |
| Wheat | 10 | 2 | 3 | 3 | 8 | 2 | 0 |
| Oats | 5 | 2 | 3 | 3 | 3 | 2 | 0 |
| Sugar beet | 10 | 10 | 10 | 10 | 10 | 10 | 10 |
| Lupins | 10 | 10 | 10 | 10 | 10 | 10 | 6 |
| Guinea grass | 10 | 10 | — | — | — | — | — |
| Japanese millet | 2 | 2 | 2 | 2 | 2 | 2 | 2 |

| | PLANT SPECIES | | | | | |
|---|---|---|---|---|---|---|
| COMPOUND NO. | PEAS | WHITE MUSTARD | BARLEY | MAIZE | LINSEED | RYEGRASS |
| 1 | 4 | 10 | 3 | 2 | 10 | 4 |
| 2 | 2 | 10 | 4 | 2 | 10 | 8 |
| 7 | 0 | 10 | 3 | — | 10 | 0 |
| 8 | 0 | 10 | 3 | — | 10 | 0 |
| 14 | 0 | 10 | 4 | 3 | 10 | 8 |
| 41 | 0 | 10 | 0 | 0 | 10 | 0 |
| 42 | 0 | 10 | 0 | 0 | 10 | 0 |
| 43 | 0 | 9 | 2 | 0 | 10 | 0 |
| 44 | 0 | 8 | 0 | 0 | 10 | 0 |
| 58 | 0 | 8 | 2 | 2 | 10 | 0 |
| 59 | 0 | 10 | 3 | 2 | 10 | 0 |

It will, of course, be appreciated that the above examples are given by way of exemplification of the invention only, and that changes may be made to the details set out therein without departing from the scope of the invention.

What is claimed is:

1. Compounds of the formula (I):

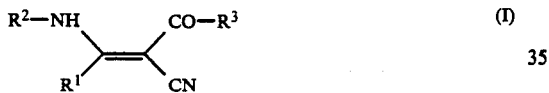

wherein, $R^1$ is a radical selected from the group consisting of alkyl, substituted alkyl substituted by one or more radicals selected from the group consisting of hydroxy, amino, N-alkylamino, N,N-dialkylamino, alkoxy and halogen, aryl and substituted aryl substituted by one or more radicals selected from the group consisting of alkyl, said substituted alkyl, halogen, hydroxy, alkoxy, amino, N-alkylamino and N,N-dialkylamino; $R^2$ is a radical of the formula (II):

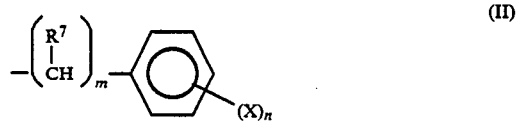

wherein, $R^7$ is a radical selected from the group consisting of hydrogen, alkyl, aralkyl and substituted aralkyl in which the aromatic or aliphatic portions are said substituted aryl or said substituted alkyl radicals respectively, m is an integer selected from the range 1 to 4, n is an integer selected from the range 1 to 3, X is a radical selected from the group consisting of hydrogen, alkyl, substituted alkyl substituted by one or more radicals selected from the group consisting of hydroxy, amino, N-alkylamino, N,N-dialkylamino, alkoxy and halogen, alkenyl, alkynyl, alkoxy, aryl, substituted aryl substituted by one or more radicals selected from the group consisting of alkyl, substituted alkyl, halogen, hydroxy, alkoxy, amino, N-alkylamino and N,N-dialkylamino, halogen, trifluoromethyl, thiocyanato, nitro, cyano, amino, carboxy, alkoxycarbonyl, thioalkyl, carbamoyl, amido, N-alkylcarbamoyl, N,N-dialkylcarbamoyl, and sulphonamido;

$R^3$ is a group of the formula (V):

$$-O(CH_2)_qY \quad (V)$$

wherein, q is an integer selected from the range 1 to 4, and Y is a radical selected from the group consisting of halogen, hydroxy, alkoxy, aryloxy, aryl, substituted aryl substituted by one or more radicals selected from the group consisting of alkyl, said substituted alkyl, halogen, hydroxy, alkoxy, amino, N-alkylamino and N,N-dialkylamino, acyloxy, thiocyanato, nitro, cyano, and amino.

2. Compounds of formula (I) as defined in claim 1, wherein, $R^1$ is selected from the group consisting of $C_1$–$C_4$ alkyl, hydroxyalkyl, alkoxyalkyl, haloalkyl, phenyl or substituted phenyl substituted by one or more radicals selected from the group consisting of hydroxy, amino, N-alkylamino, N,N-dialkylamino, alkoxy and halogen; $R^2$ is a radical of formula (II) wherein $R^7$ is selected from the group consisting of hydrogen, $C_1$–$C_4$ alkyl, benzyl substituted by one or more radicals selected from the group consisting of alkyl, said substituted alkyl, halogen, hydroxy, alkoxy, amino, N-alkylamino and N,N-dialkylamino; and X is selected from the group consisting of hydrogen, $C_1$–$C_8$ alkyl, alkenyl, alkynyl, hydroxyalkyl, alkoxyalkyl, alkoxy, phenyl, halogen, trifluoromethyl, thiocyanato, nitro, cyano, amino, carboxy, alkoxycarbonyl, carbamoyl, N-alkylcarbamoyl, N,N-dialkylcarbamoyl; $R^3$ is a group of the formula (V) wherein Y is a radical selected from the group consisting of halogen, hydroxy, alkoxy, phenoxy, substituted phenoxy in which the aromatic or aliphatic portions are said substituted aryl or said substituted alkyl radicals respectively, phenyl, substituted phenyl substituted by one or more radicals selected from the group consisting of hydroxy, amino, N-alkylamino, N,N-dialkylamino, alkoxy and halogen, thiocyanato, nitro, cyano, and amino moiety.

3. Compounds of the formula (I) as defined in claim 1, wherein $R^1$ is methyl or ethyl; $R^2$ is as defined in claim 1, and $R^3$ is a group of the formula (V) wherein q is 2 and Y is an ethoxy radical.

4. Compounds of formula (I) as defined in claim 2, wherein $R^1$ is methyl, $R^2$ is benzyl and $R^3$ is a group of the formula (V), wherein q is 2 and Y is an ethoxy radical.

5. Ethoxyethyl 2-cyano-3-dl-α-methylbenzylamino-3-ethylacrylate.

6. Ethoxyethyl 2-cyano-3-(4-chlorobenzylamino) crotonate.

7. Cyanoethyl 2-cyano-3-(4-chlorobenzylamino) crotonate.

8. Ethoxyethyl 2-cyano-3-(4-chlorobenzylamino)-3-ethylacrylate.

9. Compounds of the formula (I) as defined in claim 1, whenever prepared by a process comprising reacting a crotonic acid derivative of formula (VI):

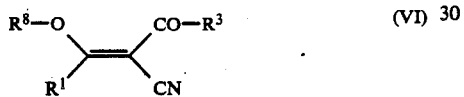

wherein $R^8$ represents methyl or ethyl, and $R^3$ is as defined in claim 1, with a compound of the formula (VII):

$R^2NH_2$ (VII)

wherein $R^2$ is as defined in claim 1.

10. A herbicidal composition comprising at least one compound of formula (I) as defined in claim 1 together with an inert carrier or diluent.

11. A method of controlling the growth of undesirable plant species which comprises applying to a plant, seed or soil an effective amount of at least one compound of formula (I) as defined in claim 1.

12. A method of controlling the growth of undesirable plant species which comprises applying to a plant, seed or soil an effective amount of a composition comprising:

(1) at least one compound of the formula (I)

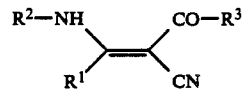

wherein, $R^1$ is a radical selected from the group consisting of alkyl, substituted alkyl substituted by one or more radicals selected from the group consisting of hydroxy, amino, N-alkylamino, N,N-dialkylamino, alkoxy and halogen, aryl and substituted aryl substituted by one or more radicals selected from the group consisting of alkyl, substituted alkyl, said substituted alkyl, halogen, hydroxy, alkoxy, amino, N-alkylamino and N,N-dialkylamino;

$R^2$ is a radical of the formula (II):

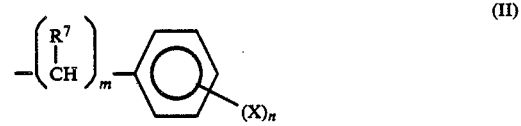

wherein,
$R^7$ is a radical selected from the group consisting of hydrogen, alkyl, aralkyl and substituted aralkyl in which the aromatic or aliphatic portions are said substituted aryl or said substituted alkyl radicals respectively, m is an integer selected from the range 1 to 4, n is an integer selected from the range 1 to 3, X is a radical selected from the group consisting of hydrogen, alkyl, substituted alkyl substituted by one or more radicals selected from the group consisting of hydroxy, amino, N-alkylamino, N,N-dialkylamino, alkoxy and halogen, alkenyl, alkynyl, alkoxy, aryl, substituted aryl substituted by one or more radicals selected from the group consisting of alkyl, substituted alkyl, halogen, hydroxy, alkoxy, amino, N-alkylamino and N,N-dialkylamino, halogen, trifluoromethyl, thiocyanato, nitro, cyano, amino, carboxy, alkoxycarbonyl, thioalkyl, carbamoyl, amido, N-alkylcarbamoyl, N,N-dialkylcarbamoyl, sulphonamido;

$R^3$ is a group of the formula (V):
—O(CH$_2$)$_q$Y (V)
wherein, q is an integer selected from the range 1 to 4, and Y is a radical selected from the group consisting of halogen, hydroxy, alkoxy, aryloxy, aryl, substituted aryl substituted by one or more radicals selected from the group consisting of alkyl, said substituted alkyl, halogen, hydroxy, alkoxy, amino, N-alkylamino and N,N-dialkylamino, acyloxy, thiocyanato, nitro, cyano, and amino moiety, and (2) an inert carrier or diluent.

* * * * *

UNITED STATES PATENT AND TRADEMARK OFFICE
CERTIFICATE OF CORRECTION

PATENT NO. : 4,935,052

DATED : June 19, 1990

INVENTOR(S) : HUPPATZ et al

It is certified that error appears in the above-identified patent and that said Letters Patent is hereby corrected as shown below:

In the Title of the invention, please change "CRONTONIC" to --CROTONIC--.

Signed and Sealed this

Seventeenth Day of September, 1991

Attest:

HARRY F. MANBECK, JR.

Attesting Officer

Commissioner of Patents and Trademarks